(12) United States Patent
Sung et al.

(10) Patent No.: US 10,098,898 B1
(45) Date of Patent: Oct. 16, 2018

(54) RELEASE STABLE MESALAMINE DOSAGE FORMS

(71) Applicant: Handa Pharmaceuticals, LLC, Fremont, CA (US)

(72) Inventors: K. C. Sung, Tainan (TW); Chi-Cheng Lin, Tainan (TW); Chin-Yao Yang, Tainan (TW); Fang-Yu Liu, Saratoga, CA (US)

(73) Assignee: HANDA PHARMACEUTICALS, LLC, San Jose, CA (US)

( * ) Notice: Subject to any disclaimer, the term of this patent is extended or adjusted under 35 U.S.C. 154(b) by 0 days.

(21) Appl. No.: 15/830,934

(22) Filed: Dec. 4, 2017

(51) Int. Cl.
*A61K 31/606* (2006.01)
*A61K 9/20* (2006.01)
*A61K 9/28* (2006.01)

(52) U.S. Cl.
CPC .......... *A61K 31/606* (2013.01); *A61K 9/2013* (2013.01); *A61K 9/2054* (2013.01); *A61K 9/2059* (2013.01); *A61K 9/282* (2013.01); *A61K 9/2813* (2013.01); *A61K 9/2846* (2013.01)

(58) Field of Classification Search
CPC .. A61K 31/606; A61K 9/2054; A61K 9/2059; A61K 9/2813; A61K 9/2846; A61K 9/282; A61K 9/2013
See application file for complete search history.

(56) References Cited

U.S. PATENT DOCUMENTS

| | | | |
|---|---|---|---|
| 4,632,921 A * | 12/1986 | Bauer | A61K 9/02 514/163 |
| 4,664,256 A | 5/1987 | Halskov | |
| 4,699,902 A | 10/1987 | Bauer | |
| 5,541,170 A | 7/1996 | Rhodes et al. | |
| 5,541,171 A | 7/1996 | Rhodes et al. | |
| 5,788,987 A | 8/1998 | Busetti et al. | |
| 6,039,975 A * | 3/2000 | Shah | A61K 9/2886 424/472 |
| 6,551,620 B2 | 4/2003 | Otterbeck | |
| 6,649,180 B1 | 11/2003 | Matsuura et al. | |
| 6,773,720 B1 | 8/2004 | Villa et al. | |
| 6,893,662 B2 | 5/2005 | Dittmar et al. | |
| 7,645,801 B2 | 1/2010 | Venkataraman et al. | |
| 8,217,083 B2 | 7/2012 | Gauthier et al. | |
| 8,337,886 B2 | 12/2012 | Otterbeck | |
| 8,436,051 B2 | 5/2013 | Gautheir et al. | |
| 8,496,965 B2 | 7/2013 | Otterbeck | |
| 8,580,302 B2 | 11/2013 | Dittmar et al. | |
| 8,865,668 B2 | 10/2014 | Raemaekers et al. | |
| 8,911,778 B2 | 12/2014 | Otterbeck et al. | |
| 8,940,328 B2 | 1/2015 | Otterbeck et al. | |
| 8,956,647 B2 | 2/2015 | Otterbeck et al. | |
| 9,089,492 B2 | 7/2015 | Dittmar et al. | |
| 2009/0028944 A1 | 1/2009 | Sathurappan et al. | |
| 2009/0169622 A1 | 7/2009 | Shukla et al. | |

FOREIGN PATENT DOCUMENTS

EP 2959892 12/2015

OTHER PUBLICATIONS

I. Khan, et al, A pH-Dependent Colon Targeted Oral Drug Delivery System Using Methacrylic Acid Copolymers I. Manipulation of Drug Release Using Eudragit L100-55 and Eudragit S100 Combinations, 58 J Control. Rel. 512 (Year: 1999).*
Moore, J.W. and Flanner, H.H. (1996), Mathematical Comparison of Curves with an Emphasis on in Vitro Dissolution Profiles. Pharmaceutical Technology, 20, 64-74.
LIALDA® (mesalamine) [package insert], Shire US Inc., by License of Nogra Pharma Limited: Lexington, MA; 2017.
Mesalamine delayed release tablets (mesalamine) [package insert], Zydus Pharmaceuticals (USA) Inc: Pennington, NJ; 2017.
U.S. Food and Drug Administration's Guidance for Industry: Bioavailability and Bioequivalence Studies for Orally Administered Drug Products—General Considerations (Aug. 2000).
Prior et al. (2003), Comparison of Dissolution Profiles: Current Guidelines, VI Congreso de la Sociedad Española de Farmacia Industrial y Galénica, y Terceras Jornadas de Tecnologia Farmacéutica(Granada), pp. 507-509.
AQUALON® (Sodium Carboxymethylcellulose), Physical and Chemical Properties, Hercules Incorporated: Wilmington, DE.
Martindale, Reynolds, Partin, Parsons, and Sweetman (1989). The Extra Pharmacopoeia, 29th Ed., pp. 1243-1249, London: Pharmaceutical Press.

* cited by examiner

*Primary Examiner* — Sean M Basquill
(74) *Attorney, Agent, or Firm* — Florek & Endres PLLC

(57) ABSTRACT

Solid oral mesalamine delayed/controlled release tablets with storage stable dissolution profiles are described.

6 Claims, No Drawings

RELEASE STABLE MESALAMINE DOSAGE FORMS

FIELD OF THE INVENTION

The present invention relates to solid mesalamine dosage forms and in particular solid controlled and/or delayed release mesalamine dosage forms that release the mesalamine in a consistent manner over time.

BACKGROUND

Mesalamine is also known as mesalazine, 5-aminosalicylic acid, and 5-amino-2-hydroxybenzoic acid, and has the following structural formula:

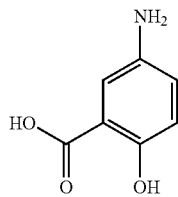

Mesalamine is an anti-inflammatory that is often used to treat inflammatory bowel disease such as ulcerative colitis and Crohn's disease.

Mesalamine is commercially available in the United States under a variety of trade names and dosage forms such as CANASA® (suppository), ROWASA® (enema), DELZICOL® (delayed release capsule), APRISO® (extended release capsule), PENTASA® (extended release capsule), ASACOL® and ASACOL® HD (delayed release capsule), and LIALDA® (delayed release tablet). Some patents that have been identified as covering these commercial mesalamine products include U.S. Pat. Nos. 5,541,170; 5,541,171; 6,551,620; 6,649,180; 6,773,720; 6,893,662; 7,645,801; 8,217,083; 8,337,886; 8,436,051; 8,496,965; 8,580,302; 8,865,668; 8,911,778; 8,940,328; 8,956,647; and 9,089,492.

It is believed that mesalamine is topically active in the lower gastrointestinal region and in particular in the terminal ileum, colon, and rectal region. Therefore, oral dosage forms are designed to release the mesalamine in these regions, usually by use of a delayed release coating, sometimes referred to as an enteric coating. Some oral dosage forms have also attempted to provide a controlled release of mesalamine in the target regions by employing a controlled release excipient in conjunction with the delayed release coating. However, these controlled/delayed release dosage forms have problems. For example it has been discovered that the LIALDA® product, which employs a tablet core matrix comprising mesalamine and sodium carboxymethylcellulose that is coated with an enteric coating, exhibits a faster release of the drug after storage under accelerated conditions, such as at 40° C. and at 75% relative humidity. This storage fluctuation may have adverse effects on drug release because it may cause large amounts of the drug to be released prematurely, i.e. released not at the target area, or excess amounts of the drug released too fast in the target area which may lead to adverse effects such as major fluctuations of therapeutic levels of the drug between dosing intervals.

The amount of mesalamine dosed orally is often very high. For example, the dosing for the LIALDA® tablet is two to four tablets administered once a day, wherein each tablet contains 1.2 grams (1200 mg) of mesalamine. Due to the large dosing requirements, the formulation of solid oral dosage forms of mesalamine is difficult because the amount of excipients that may be incorporated into a tablet or capsule must be kept to a minimum to allow the dosage form to be easily swallowed, and to keep the number of dosage forms per administration to a minimum number, i.e. less than 4 dosage forms per administration.

SUMMARY OF THE INVENTION

The present invention is a solid oral dosage form, preferably in the form of a tablet, that allows for a consistent drug release profile over time.

One embodiment of the present invention is a controlled release tablet comprising mesalamine, a controlled release excipient, and a buffering/basifying agent wherein the release of the mesalamine from the controlled release tablet is substantially constant when stored for a period of time including under accelerated storage conditions of elevated temperature and humidity. In certain aspects, the controlled release tablet is a controlled release matrix tablet wherein the matrix comprises mesalamine, a controlled release matrix forming excipient, and a buffering/basifying agent. In another aspect, the controlled release tablet may further comprise an enteric material, preferably an enteric coating surrounding the controlled release tablet, and most preferably an enteric coating surrounding the controlled release matrix tablet. In a further aspect, the controlled release excipient or controlled release matrix forming excipient is a polymer.

Another embodiment of the present invention, comprises a method for making a release stable mesalamine controlled release tablet comprising the steps of forming a blend, preferably a homogeneous or uniform blend, of the mesalamine, a controlled release excipient, and a buffering/basifying agent, and compressing the blend into a core. The method may further comprise the step of coating the core with a delayed release coating. In some embodiments the blend may further comprise one or more pharmaceutically acceptable excipients such as a binder, a filler, a disintegrant, a lubricant, a glidant, a solubilizing agent, a plasticizer, a coloring agent, an antioxidant, a chelating agent, and combinations thereof.

A further embodiment of the present invention also includes a method for treating inflammatory bowel disease, including ulcerative colitis and Crohn's disease, comprising the oral administration of the release stable mesalamine solid dosage forms of the present invention.

DETAILED DESCRIPTION OF THE INVENTION

Before the present invention is further described, it is to be understood that this invention is not limited to the particular embodiments described. It is also to be understood that the terminology used herein is for the purpose of describing particular embodiments only, and is not intended to be limiting.

It should be noted that as used herein, the singular forms "a," "an," and "the" include plural referents unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

"Immediate Release" refers to a dosage form or component thereof that releases, or delivers about 100% of the one or more pharmaceutical agents or drugs in one hour or less, preferably in 45 minutes or less, and most preferably in 30 minutes or less following administration to a subject or when tested using known in vitro testing apparatus such as those described in the United States Pharmacopeia section <711> Dissolution and <724> Drug Release.

"Modified release" refers to a dosage form or component thereof that releases or delivers one or more pharmaceutical agents or drugs in a manner other than immediate release. Modified release includes, pulsatile release, delayed release, controlled release, sustained release, extended release, or a combination thereof.

"Delayed release" refers to a dosage form or component thereof that releases or delivers one or more pharmaceutical agents or drugs after a predetermined period of time following administration to a subject or when tested using known in vitro testing apparatus such as those described in the United States Pharmacopeia section <711> Dissolution and <724> Drug Release. Examples of delayed release dosage forms include dosage forms that release or deliver the pharmaceutical agent or drug when placed into a specific pH environment, i.e. a pH dependent release such as an enteric coated tablet or capsule.

"Controlled release" (also known as CR), "Sustained release" (also known as SR), and "Extended release" (also known as ER), are used synonymously herein and refer to a pharmaceutical formulation or component thereof that releases or delivers one or more pharmaceutical agents or drugs over a prolonged period of time, such as over 2 hours, 3 hours, 4 hours, 5 hours, 6 hours, 8 hours, 10 hours, 12 hours, 14 hours, 16 hours, 18 hours, 20 hours, or 24 hours following administration to a subject or when tested using known in vitro testing apparatus such as those described in the United States Pharmacopeia section <711> Dissolution and <724> Drug Release.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the term "release stable" means a dosage form that releases the drug in a substantially constant manner before and after storage. The release of the drug may be measured by any conventional methods known in the pharmaceutical arts, including those described in the United States Pharmacopeia (USP), United States Pharmacopeia section <711> Dissolution and <724> Drug Release. The preferred methods include the USP dissolution methods that employ Apparatus I (basket) or Apparatus II (paddle). One preferred method for measuring the drug release is to employ USP Apparatus II (paddle), 900-1,000 mL of an aqueous phosphate buffer with a pH of 7.2, 37° C., and 100 rpm.

As used herein the term "substantially constant" when used to modify the in vitro drug release may mean that no measured value of the in vitro release profile before and after storage under accelerated storage conditions differs by more than 30 percentage points, by no more than 25 percentage points, by no more than 20 percentage points, by no more than 15 percentage points, by no more than 12 percentage points, and by no more than 10 percentage points. For example, if a mesalamine dosage form exhibits a 3 hour release of 50% mesalamine before storage and a 3 hour release of 82% mesalamine after storage under accelerate conditions, the dosage form would not exhibit a substantially constant release profile because the difference between 3 hours before storage and 3 hours after storage is 32 percentage points (82%-50%=32). Similarly, if a mesalamine dosage form exhibits a 2 hour release of 25% mesalamine before storage and a 2 hour release of 33% mesalamine after storage under accelerate conditions, the dosage form would exhibit a substantially constant release profile because the difference between 2 hours before storage and 2 hours after storage is 8 percentage points (33%-25%=8).

As used herein the term "substantially constant" when used to modify the in vitro drug release may alternatively mean that the similarity factor ($f_2$) of the in vitro drug release profile before and after storage is 50 or greater, 60 or greater, 70 or greater, 75 or greater, 80 or greater, 85 of greater, 90 or greater, or 95 or greater. The $f_2$ may be determined by the following equation:

$$f_2 = 50 \cdot \log\{[1+(1/n)\Sigma_{t=1}^{n}(R_t-T_t)^2]^{-0.5} \cdot 100\}$$

wherein $R_t$ is the mean percent of drug released for the reference product or initial time of testing and $T_t$ is the mean percent of drug released for the test product or after storage. In certain embodiments, the $f_2$ value is determined using the mean percent of twelve (12) dosage units and a minimum of three time points and not more than one mean value greater than 85%. A more detailed description of the similarity factor ($f_2$) can be found in Moore et al., "Mathematical Comparison of Curves with an Emphasis on in Vitro Dissolution Profiles," *Pharmaceutical Technology*, (1996) 20, pp. 64-74, and the U.S. FDA's Guidance for Industry, *Waiver of In Vivo Bioavailability and Bioequivalence Studies for Immediate-Release Solid Oral Dosage Forms based on a Biopharmaceutics Classification System*. August 2000.

As used herein accelerated storage conditions means the dosage form is stored at a temperature above room temperature and at 50% relative humidity for at least 24 hours. Some examples of accelerated storage conditions include, but are not limited to 30° C. and 75% relative humidity; 40° C. and 75% relative humidity; and 60° C. and 75% relative humidity. The dosage form may be stored under these conditions for an appropriate time period such as 2 days, 5 days, 7 days, 14 days, 28 days, 84 days, or longer. In certain embodiments, the dosage forms are stored in an opaque child-resistant screw capped high density polyethylene bottle with or without an aluminum seal. In certain embodiments, 1 to 120 units of the dosage forms, preferably 2 to 60 units of the dosage forms and most preferably 3 to 30 units of the dosage forms will be stored in a 70-240 cc, preferably 100-150 cc, opaque child-resistant screw capped high density polyethylene bottle with an aluminum seal.

The controlled release tablet of the present invention comprises:
 a) mesalamine;
 b) a controlled release excipient; and
 c) a buffering/basifying agent.

In certain aspects of this embodiment, the controlled release excipient is a polymeric material. The controlled release tablets of the present invention may further comprise one or more additional pharmaceutical excipients including but not limited to a binder, a filler, a disintegrant, a lubricant, a glidant, a solubilizing agent, a plasticizer, a coloring agent, an antioxidant, a chelating agent, and combinations thereof. Other excipients that may be included can be found in the Handbook of Pharmaceutical Excipients, 6$^{th}$ ed. (2009).

In certain embodiments of the present invention, the controlled release tablets are a matrix tablet comprising a compressed mixture of:
  a) mesalamine;
  b) a controlled release excipient;
  c) a buffering/basifying agent; and
  d) one or more additional pharmaceutical excipients including but not limited to a binder, a filler, a lubricant, a glidant, a solubilizing agent, a plasticizer, a coloring agent, an antioxidant, a chelating agent and combinations thereof.

The weight percentages of the various ingredients of certain embodiments of the tablet prepared in accordance with the present invention are shown in the following table:

| Ingredient | Embodiment A Wt % Range | Embodiment B Wt % Range | Embodiment C Wt % Range |
| --- | --- | --- | --- |
| Mesalamine | 50-99 | 60-98 | 70-97 |
| Controlled Release Excipient | 0.5-25 | 1-20 | 1.5-15 |
| Buffering/Basifying Agent | 0.1-15 | 0.25-10 | 0.5-7.5 |
| Pharmaceutical Excipients | 0-30 | 0-25 | 0-20 |

The values in the above table are based on the total weight of the compressed uncoated tablet.

Examples of controlled release excipients that may be employed in the tablets of the present invention are pharmaceutical excipients that delay and/or control the release of the drug from the tablet when tested using an USP dissolution apparatus. In certain aspects of this embodiment, the controlled release excipient is a polymeric material. Examples of the controlled release excipients include: a hydrophilic polymer; a water soluble polymer; a hydrophobic polymer; a water-insoluble polymer; a wax; a clay; or a combination thereof. Preferred examples of the controlled release excipients include a hydrophilic or gelling polymer. Suitable hydrophilic or gelling polymers include, without limitation, polyalkylene oxides, particularly poly(ethylene oxide), polyethylene glycol, and poly(ethylene oxide)-poly(propylene oxide) copolymers; cellulosic polymers, such as methylcellulose, hydroxymethyl cellulose, hydroxyethyl cellulose, hydroxypropyl cellulose, hydroxypropyl methylcellulose, carboxymethyl cellulose and salts thereof, microcrystalline cellulose, and polysaccharides and their derivatives; acrylic acid and methacrylic acid polymers, copolymers, and esters thereof, preferably formed from acrylic acid; methacrylic acid; methyl acrylate; ethyl acrylate; methyl methacrylate; ethyl methacrylate; and copolymers thereof; with each other or with additional acrylate species such as aminoethyl acrylate; maleic anhydride copolymers; polymaleic acid; poly(acrylamides) such as polyacrylamide per se, poly(methacrylamide), poly(dimethylacrylamide), and poly(N-isopropyl-acrylamide); polyalkylene oxides; poly(olefinic alcohol)s such as poly(vinyl alcohol); poly(N-vinyl lactams) such as poly(vinyl pyrrolidone), poly(N-vinyl caprolactam), and copolymers thereof; polysaccharide gums such as xanthan gum, and guar gum; carrageenan; starches; and alginates. Some of the preferred hydrophilic or gelling polymers include but are not limited to polyethylene oxide, hydroxypropyl cellulose, hydroxypropyl methylcellulose, carbomers (i.e. acrylic acid polymers or Carbopol), carboxymethylcellulose calcium, carboxymethylcellulose sodium, croscarmellose sodium, carrageenan, xanthan gum, guar gum, sodium alginate, and calcium alginate.

In one embodiment, the hydrophilic or gelling polymer(s) may be a cellulosic polymer, such as an alkyl substituted cellulose derivative. In one embodiment, the polymer is an alkyl substituted cellulose having a viscosity within the range of about 100 to about 110,000 centipoise as a 2% aqueous solution at 20° C. In another embodiment, the polymer is an alkyl substituted cellulose having a viscosity within the range of about 1,000 to about 4,000 centipoise as a 1% aqueous solution at 20° C. Preferred alkyl celluloses are hydroxypropyl cellulose and hydroxypropyl methylcellulose.

In one embodiment, the hydrophilic or gelling polymer(s) may be a polyalkylene oxide. In another aspect, the polyalkylene oxide may be a polyethylene oxide. In an embodiment, the polyethylene oxide may have an approximate molecular weight between 100,000 Daltons (Da) to about 10,000,000 Da or about 500,000 Da to about 7,000,000 Da. In a further embodiment, the polyethylene oxide may have a molecular weight of approximately 600,000 Da, 700,000 Da, 800,000 Da, 900,000 Da, 1,000,000 Da, 2,000,000 Da, 3,000,000 Da, 4,000,000 Da, 5,000,000 Da, 6,000,000 Da, 7,000,000 Da, 8,000,000 Da 9,000,000 Da, or 10,000,000 Da.

In one embodiment, the hydrophilic or gelling polymer(s) may be a carboxymethylcellulose or salts thereof. Preferred carboxymethylcelluloses are alkali or alkali earth metal salts and include carboxymethylcellulose sodium, carboxymethylcellulose potassium carboxymethylcellulose calcium, carboxymethylcellulose magnesium, and combinations thereof.

In certain embodiments of the present invention, the controlled release excipient should be present in an amount sufficient to control the release of the mesalamine from the tablet for a period of about 4 to about 12 hours when tested in a suitable USP dissolution apparatus. In certain embodiments of the present invention, the controlled release excipient should be present in an amount so the mesalamine is released from the tablet according the following release profiles when the tablet comprising the mesalamine, controlled release excipient and buffering/basifying agent is tested in a USP Apparatus II at 37° C., 100 rpm, and 900-1,000 mL of an aqueous pH 7.2 phosphate buffer solution:

| Time | Preferred Release % | Most Preferred Release % |
| --- | --- | --- |
| 1 hour | 0-40 | 5-30 |
| 2 hour | 10-70 | 15-65 |
| 3 hour | 25-90 | 35-85 |
| 4 hour | 35-100 | 40-100 |

The above in vitro release profile ranges are examples of preferred controlled release profile ranges and not release stability or a substantially constant release profile.

The buffering/basifying agent should be present in the tablet of the present invention in an amount that is sufficient to maintain a substantially constant release of the mesalamine from the tablet after storage under accelerated conditions. Research has shown that the buffering/basifying agent should exhibit one or more of the following properties:
 (i) exhibit a pH of at least 6.0 or higher, at least 7.0 or higher, or at least 7.5 or higher when a 10% aqueous solution is prepared with the buffering/basifying agent;
 (ii) exhibit a pKa of at least 6.0 or higher, at least 7.0 or higher, or at least 8.0 or higher; or
 (iii) both (i) and (ii).

The buffering/basifying agent may be an inorganic or organic compound. Examples of buffering/basifying agents that may be used in the present invention include but are not limited to amino acids such as arginine and lysine, boric acid, calcium carbonate, calcium hydroxide, calcium lactate, calcium phosphate, diethanolamine, methionine, monoethanolamine, monosodium glutamate, meglumine, potassium acetate, potassium bicarbonate, potassium borate, potassium carbonate, potassium citrate, potassium hydroxide, potassium lactate, potassium phosphate, sodium acetate, sodium bicarbonate, sodium borate, sodium carbonate, sodium citrate, sodium hydroxide, sodium lactate, sodium phosphate including sodium phosphate monobasic, and sodium phosphate dibasic, triethanolamine, or combinations thereof.

The amount of buffering/basifying agent employed in the tablets of the present invention should be sufficient to create a basic tablet excipient pH. As used herein the term "a basic tablet excipient pH" means the combination of excipients without mesalamine, employed in the tablet, when placed in a 50 mL volumetric flask and mixed with sufficient water to the volume (i.e., 50 mL) exhibit a pH of at least 7.0 or higher, a pH of 7.25 or higher, a pH of 7.5 or higher, a pH of 7.75 or higher, a pH of 8.0 or higher, a pH of 8.2 or higher, a pH of 8.5 or higher, or a pH of 8.75 or higher. For example, a tablet prepared in accordance with the present invention may have the following composition:

| | |
|---|---|
| Mesalamine | 1200 mg |
| Sodium Carboxymethylcellulose | 40 mg |
| Sodium Starch Glycoloate | 10 mg |
| Magnesium Stearate | 10 mg |
| Disodium Hydrogen Phosphate | 60 mg |
| Total | 1320 mg |

The disodium hydrogen phosphate is a buffering/basifying agent because a 1% aqueous solution exhibits a pH of about 9.1 and has the following pKa values 2.15, 7.20, and 12.38. In addition, placing the equivalent of two tablet excipients (i.e., 80 mg sodium carboxymethylcellulose, 20 mg sodium starch glycolate, 20 mg magnesium stearate, and 120 mg of disodium hydrogen phosphate in a 50 mL volumetric flask and adding deionized water to volume produces a pH of 8.91 which is an example of "a basic tablet excipient pH" as used herein.

Examples of binders that may be employed in the tablets of the present invention include but are not limited to acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. Preferably, the binder is selected from povidone, povidone derivative, polyvinyl alcohol, hypromellose, hydroxypropyl cellulose, hydroxyethyl cellulose, polymethacrylates, methyl cellulose, gelatin and ethyl cellulose, or mixtures thereof. Especially preferred binders include water soluble binders such as povidone, hypromellose, hydroxypropyl cellulose, gelatin, and mixtures thereof. If the binder is a polymeric binder, it is preferred that the binder has a low molecular weight and/or exhibit a viscosity of less than 200 mPa s, preferably less than 100 mPa s, and most preferably less than 50 mPa s when tested at a concentration of 2% (w/v) aqueous preparation at 20° C.

Examples of fillers that may be employed in the tablets of the present invention include but are not limited to lactose, sucrose, mannitol, sorbitol, dextrose, dextrin, maltose, xylitol, maltitol, lactitol, erythritol, isomalt, microcrystalline cellulose, powdered cellulose, silicified microcrystalline cellulose, starch, and mixtures thereof.

Examples of disintegrants that may be employed in the tablets of the present invention include but are not limited to croscarmellose sodium, starch, crospovidone (polyplasdone XL-10), sodium starch glycolate (EXPLOTAB® or PRIMOJEL®) and mixtures thereof.

Examples of lubricants that may be employed in the tablets of the present invention include but are not limited to magnesium stearate, sodium stearyl fumarate, stearic acid, glyceryl behenate, polyethylene glycols (preferably wherein the polyethylene glycol has a molecular weight of 6000 or more), polyoxyethylene stearate, magnesium lauryl sulfate, sodium oleate, and mixtures thereof.

Examples of glidants that may be employed in the tablets of the present invention include but are not limited to colloidal silicon dioxide, corn starch, talc, and mixtures thereof.

Examples of solubilizing agents that may be employed in the tablets of the present invention include but are not limited to cyclodextrins, surfactants (sometimes referred to as wetting agents), and mixtures thereof. The cyclodextrin may be an alpha, beta, or gamma type cyclodextrin; alpha, beta, or gamma type cyclodextrin derivatives; or a combination thereof. The surfactant may be a non-ionic surfactant, an ionic surfactant, or a combination thereof. Examples of non-ionic surfactants include polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, a polyoxypropylene fatty acid ester, or a mixture of the foregoing. A further listing of possible non-ionic surfactants can be found on pages 1243-1249 of Martindale, *The Extra Pharmacopoeia* $29^{th}$ ed., which is incorporated herein by reference. Examples of ionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, phosphates, quaternary ammonium salts, ethoxylated amines, aluminum monostearate, calcium stearate, sulfated castor oil, sodium cetostearyl sulfate, sodium lauryl sulfate, sodium oleate, potassium oleate, zinc oleate, sodium stearate, sodium tetradecyl sulfate, and mixtures therefore.

Examples of plasticizers that may be used in the tablets of the present invention include but are not limited to adipate, azelate, enzoate, citrate, stearate, isoebucate, sebacate, triethyl citrate, tri-n-butyl citrate, acetyl tri-n-butyl citrate, citric acid esters, and those described in the *Encyclopedia of*

*Polymer Science and Technology*, Vol. 10 (1969), published by John Wiley & Sons, which is incorporated in its entirety herein by reference.

Examples of coloring agents that may be employed in the tablets of the present invention include but are not limited to FD&C-type dyes and lakes, fruit and vegetable extracts, titanium dioxide and mixtures thereof.

Examples of antioxidants that may be employed in the tablets of the present invention include but are not limited to ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate, or combinations thereof.

Examples of chelating agents that may be employed in the tablets of the present invention include but are not limited to ethylenediaminetetraacetic acid (EDTA) and its derivatives, thioglycolic acid, thiolactic acid, thioglycerol, and the like, or combinations thereof.

The tablets of the present invention may be coated with aesthetic and or functional coatings. In certain embodiments of the present invention, the tablets may be coated with a delayed release or enteric coating.

The delayed release or enteric coating may comprises (i) at least one enteric material; (ii) optionally a water soluble or insoluble film forming polymer; and (iii) optionally at least one pharmaceutically acceptable excipient such as a lubricant, glidant, plasticizer, solubilizing agent, coloring agent, or combination thereof. Examples of lubricants, glidants, plasticizers, and solubilizing agents are provided above. Two or more delayed release or enteric coatings may be applied to the tablets prepared in accordance with the present invention.

The enteric material employed in the delayed release or enteric coating is a material that exhibits a pH dependent solubility. In certain embodiments the enteric material is insoluble when exposed to an aqueous environment with pH below 5.0 but soluble at a pH of 5.0 or higher, preferably is insoluble when exposed to an aqueous environment with pH below 6.0 but soluble at a pH of 6.0 or higher, and most preferably is insoluble when exposed to an aqueous environment with pH below 7.0 but soluble at a pH of 7.0 or higher. Examples of enteric materials that may be employed in the release coating(s) include hypromellose phthalate, cellulose acetate phthalate, carboxymethyl ethyl cellulose, methyl methacrylate-methacrylic acid copolymer, methacrylic acid-ethyl acrylate copolymer, methacrylic acid-methyl acrylate-methyl methacrylate copolymer, hydroxypropyl methylcellulose acetate succinate, polyvinyl acetate phthalate, shellac, and the like. Specific examples of commercially available products include polymers such as hypromellose phthalate (HP-55, HP-50, manufactured by Shin-Etsu Chemical Co., Ltd.), cellulose acetate phthalate, carboxymethyl ethyl cellulose (CMEC, manufactured by Freund Corporation), methyl methacrylate-methacrylic acid copolymer (Eudragit L 100 (methacrylic acid copolymer L) or Eudragit S 100 (methacrylic acid copolymer S) manufactured by Evonik Roehm), methacrylic acid-ethyl acrylate copolymer (Eudragit L 100-55 (dried methacrylic acid copolymer LD) or Eudragit L 30 D-55 (methacrylic acid copolymer LD) manufactured by Evonik Roehm), methacrylic acid-methyl acrylate-methyl methacrylate copolymer (Eudragit FS 30 D, manufactured by Evonik Roehm), hydroxypropyl methylcellulose acetate succinate (HPM-CAS manufactured by Shin-Etsu Chemical Co., Ltd.), polyvinyl acetate phthalate, shellac, and the like. Preferred examples of enteric polymers are polymers comprising methacrylic acid monomers such as methyl methacrylate-methacrylic acid copolymer, methacrylic acid-ethyl acrylate copolymer, methacrylic acid-methyl acrylate-methyl methacrylate copolymer, and combinations thereof. Examples of the enteric polymer include, but are not limited to Eudragit L 100, Eudragit S 100, Eudragit L 100-55, Eudragit L 30 D-55, Eudragit FS 30 D, and mixtures thereof.

In certain embodiments, the delayed release or enteric coating comprises a mixture of two or more enteric materials, preferably a mixture of Eudragit S 100 (methacrylic acid copolymer S), Eudragit L 100 (methacrylic acid copolymer L), and Eudragit FS 30 D (methacrylic acid-methyl acrylate-methyl methacrylate copolymer).

A water soluble or insoluble film forming polymer may be incorporated into the delayed release or enteric coating to adjust the release rate of the final coated tablet to a desired release profile.

Examples of water soluble film forming polymers that may be employed in the delayed release or enteric coating include but are not limited to povidone, hypromellose, hydroxypropyl cellulose, hydroxyethyl cellulose, povidone derivative, polyvinyl alcohol, or mixtures thereof. Especially preferred water soluble film forming polymers include water soluble binders as discussed above such as povidone, hypromellose, hydroxypropyl cellulose, gelatin, and mixtures thereof. The water soluble film forming polymer should have a low molecular weight and/or exhibit a viscosity of less than 200 mPa s, preferably less than 100 mPa s, and most preferably less than 50 mPa s when tested at a concentration of 2% (w/v) aqueous preparation at 20° C. Some of the preferred binders include PHARMACOAT 606 and PHARMACOAT 603 (hypromellose with viscosity at 20° C. and 2% aqueous solution of 6 cps and 3 cps respectively, commercially available from Shin-Etsu Chemicals); METHOCEL E3, E5, E6, E15 and E50 (hypromellose with viscosity at 20° C. and 2% aqueous solution of 3, 5, 6, 15 and 50 cps respectively, commercially available from Dow Chemical); KLUCEL EF and KLUCEL LF, (hydroxypropyl cellulose, commercially available from Aqualon); LH-11, LH-20, LH-21, LH-22, LH-30, LH-31, and LH-32 (low-substituted hydroxypropyl cellulose, commercially available from Shin-Etsu Chemical); and KOLLIDON (povidone).

Examples of water insoluble film forming polymers that may be employed in the delayed release or enteric coating include but are not limited to celluloses such as ethylcellulose, cellulose acetate, cellulose acetate butyrate, polyvinyl acetate, and polymethacrylates such as copolymers of ethyl acrylate and methyl methacrylate, and combinations thereof. Commercial examples of water insoluble film forming polymers are available under the trade name SURERELEASE, AQUACOAT, EUDRAGIT RS, EUDRAGIT RL, EUDRAGIT NE 30 D, EUDRAGIT NE 40 D. Preferred water insoluble film forming polymers are ethylcellulose, cellulose acetate, polyvinyl acetate, or mixtures thereof.

One or more seal coatings may also be applied to the tablets of the present invention prior to application of the delayed release or enteric coating. The seal coating(s) will protect the tablet core from contacting any acidic components in the subsequently applied delayed release or enteric coating(s) and should prevent any interaction between the tablet core material and the components of the delayed release or enteric coating. The seal coating(s) may be water soluble or rapidly dispersible when exposed to an aqueous environment.

The tablets of the present invention may also comprise a final aesthetic, polishing, or color coating if desired. In addition to providing an improved aesthetic appearance, final aesthetic, polishing or color coating may also provide an anti-sticking function. The final aesthetic, polishing, or color coating should be water soluble or rapidly dispersible when exposed to an aqueous environment and should not affect the release properties of the tablet.

The tablets of the present invention may be prepared by any methods commonly used in the pharmaceutical arts to prepare the tablets such as dry blending the ingredients of the tablet or granulating all or part of the ingredients of the tablets prior to compression into a tablet. If a granulation step is employed, the granules may be prepared by extrusion or by dry granulation or by wet granulation techniques. A dry granulation technique may include a slugging step, and/or roller compaction step, and a subsequent milling step. If a wet granulation technique is employed, the wet granules should be prepared and dried before being added to the tablet die.

If a delayed release or enteric coating, seal coating, or aesthetic coating is applied to compressed tablets of the present invention, the coatings may also be applied by any method commonly used in the pharmaceutical arts such as pan coating or fluidized bed coating.

If not otherwise defined, the test methods referred to herein are to be conducted in accordance to the general chapters of the United States Pharmacopeia (USP) 40 (2017) which are incorporated herein by reference:

The dissolution and drug release testing is to be conducted using the method and apparatus described in USP 40 General Chapter section <711> Dissolution and <724> Drug Release.

The pH is to be conducted using the method and apparatus described in USP General Chapter <791> pH.

DESCRIPTION OF THE PREFERRED EMBODIMENTS

In one embodiment of the present invention there is provided a mesalamine tablet comprising:
(a) about 50 wt % to about 99 wt %, preferably about 60 wt % to about 98 wt %, and most preferably about 70 wt % to about 97 wt % of mesalamine;
(b) about 0.5 wt % to about 25 wt %, preferably about 1 wt % to about 20 wt %, and most preferably about 1.5 wt % to about 15 wt % of a controlled release excipient selected from a hydrophilic or gelling polymer, preferably a gelling polymer selected from the group consisting of polyethylene oxide, hydroxypropyl cellulose, hydroxypropyl methylcellulose, carbomers, carboxymethylcellulose calcium, carboxymethylcellulose sodium, croscarmellose sodium, carrageenan, sodium starch glycolate, xanthan gum, guar gum, sodium alginate, calcium alginate, or mixtures thereof;
(c) about 0.1 wt % to about 15 wt %, preferably about 0.25 wt % to about 10 wt %, and most preferably about 0.5 wt % to about 7.5 wt % of a buffering/basifying agent wherein the buffering/basifying agent exhibits one or more of the following properties: (i) a pH of at least 7.0 or higher, at least 7.5 or higher when a 10% aqueous solution is prepared with the buffering/basifying agent; (ii) exhibits a pKa of at least 7.0 or higher, at least 8.0 or higher; or (iii) a combination of (c)(i) and (c)(ii);
(d) optionally one or more pharmaceutical excipients selected from the group consisting of a binder, a filler, a lubricant, a glidant, a solubilizing agent, a plasticizer, a coloring agent, an antioxidant, a chelating agent, or combinations thereof; and
(e) optionally a delayed release or enteric coating surrounding the tablet;
wherein the tablet exhibits an in vitro release profile before and after storage of the tablet, in an opaque child-resistant screw capped HDPE bottle with or without an aluminum foil seal, at 60° C. and 75% relative humidity for at least two days or longer, or at 40° C. and 75% relative humidity for at least 28 days or longer, preferably at least 84 days or longer that differs by no more than 30 percentage points, by no more than 25 percentage points, by no more than 20 percentage points, by no more than 15 percentage points, by no more than 12 percentage points, and by no more than 10 percentage points at 1 hour, 2 hours, 3 hours, and/or 4 hours of testing when tested with a USP Apparatus II (paddle), 900-1,000 mL of an aqueous phosphate buffer with a pH of 7.2, 37° C., and 100 rpm.

In an alternative aspect of this embodiment the tablet exhibits a similarity factor ($f_2$) of the in vitro drug release profile before and after storage of 50 or greater, of 55 or greater, of 60 or greater, of 65 or greater, or of 70 or greater.

In another embodiment of the present invention there is provided a mesalamine tablet comprising:
(a) about 60 wt % to about 98 wt %, and preferably about 70 wt % to about 97 wt % of mesalamine;
(b) about 1 wt % to about 20 wt %, and preferably about 1.5 wt % to about 15 wt % of a controlled release excipient selected from carboxymethylcellulose calcium, carboxymethylcellulose sodium, croscarmellose sodium, carrageenan, hydroxypropyl cellulose, hydroxypropyl methylcellulose, xanthan gum, guar gum, sodium alginate, calcium alginate, or mixtures thereof;
(c) about 0.25 wt % to about 10 wt %, and preferably about 0.5 wt % to about 7.5 wt % of a buffering/basifying agent wherein the buffering/basifying agent exhibits: (i) a pH of at least 7.5 or higher when a 10% aqueous solution is prepared with the buffering/basifying agent and (ii) exhibits a pKa of at least 8.0 or higher;
(d) optionally one or more pharmaceutical excipients selected from the group consisting of a binder, a filler, a lubricant, a glidant, a solubilizing agent, a plasticizer, a coloring agent, an antioxidant, a chelating agent, or combinations thereof; and
(e) a delayed release or enteric coating surrounding the tablet;
wherein the tablet exhibits an in vitro release profile before and after storage of the tablet, in an opaque child-resistant screw capped HDPE bottle with or without an aluminum foil seal, at 40° C. and 75% relative humidity for at least 84 days or longer, that differs by no more than 20 percentage points, by no more than 15 percentage points, by no more than 12 percentage points, and by no more than 10 percentage points at 1 hour, 2 hours, 3 hours, and/or 4 hours of testing when tested with a USP Apparatus II (paddle), 900-1,000 mL of an aqueous phosphate buffer with a pH of 7.2, 37° C., and 100 rpm.

In an alternative aspect of this embodiment the tablet exhibits a similarity factor ($f_2$) of the in vitro drug release profile before and after storage of 50 or greater, of 55 or greater, of 60 or greater, of 65 or greater, or of 70 or greater.

In further embodiment of the present invention there is provided a mesalamine tablet comprising:
(a) about 70 wt % to about 97 wt % of mesalamine;
(b) about 1.5 wt % to about 15 wt % of a controlled release excipient selected from carboxymethylcellulose calcium, carboxymethylcellulose sodium or mixtures thereof;
(c) a buffering/basifying agent wherein the buffering/basifying agent exhibits: (i) a pH of at least 7.0 or higher, at least 7.5 or higher when a 10% aqueous solution is prepared with the buffering/basifying agent; (ii) exhibits a pKa of at least 7.0 or higher, at least 8.0 or higher; or (iii) a combination of (c)(i) and (c)(ii) and the buffering/basifying agent is present in the tablet in an amount to create a basic tablet excipient pH of 7.5 or higher, of 7.75 or higher, of 8.0 or higher, of 8.2 or higher, of 8.5 or higher, or of 8.75 or higher when the combination of excipients employed in the tablet without the mesalamine and without any coating material is placed in a 50 mL volumetric flask, mixed with sufficient water to volume (i.e., 50 mL);
(d) optionally one or more pharmaceutical excipients selected from the group consisting of a binder, a filler, a lubricant, a glidant, a solubilizing agent, a plasticizer, a coloring agent, an antioxidant, a chelating agent, or combinations thereof; and
(e) optionally a delayed release or enteric coating surrounding the tablet;
wherein the tablet exhibits an in vitro release profile before and after storage of the tablet, in an opaque child-resistant screw capped HDPE bottle with or without an aluminum foil seal, at 60° C. and 75% relative humidity for at least two days or longer, or at 40° C. and 75% relative humidity for at least 28 days or longer, preferably at least 84 days or longer that differs by no more than 30 percentage points, by no more than 25 percentage points, by no more than 20 percentage points, by no more than 15 percentage points, by no more than 12 percentage points, and by no more than 10 percentage points at 1 hour, 2 hours, 3 hours, and/or 4 hours of testing when tested with a USP Apparatus II (paddle), 900-1,000 mL of an aqueous phosphate buffer with a pH of 7.2, 37° C., and 100 rpm.

In an alternative aspect of this embodiment the tablet exhibits a similarity factor ($f_2$) of the in vitro drug release profile before and after storage of 50 or greater, of 55 or greater, of 60 or greater, of 65 or greater, or of 70 or greater.

In still further embodiment of the present invention there is provided a mesalamine tablet comprising:
(a) about 60 wt % to about 98 wt %, and preferably about 70 wt % to about 97 wt % of mesalamine;
(b) about 1 wt % to about 20 wt %, and preferably about 1.5 wt % to about 15 wt % of a controlled release excipient selected from carboxymethylcellulose calcium, carboxymethylcellulose sodium, or mixtures thereof;
(c) a buffering/basifying agent selected from the group consisting of alkali or alkali metal salts of acetic acid, citric acid, phosphoric acid, alkali or alkali metal hydroxides, alkali or alkali metal carbonate salts, alkali or alkali metal bicarbonate salts, meglamine, triethanolamine, amino acids, or combinations thereof wherein the buffering/basifying agent exhibits: (i) a pH of at least 7.0 or higher, at least 7.5 or higher when a 10% aqueous solution is prepared with the buffering/basifying agent; and (ii) a pKa of at least 7.5 or higher, at least 8.0 or higher; and the buffering/basifying agent is present in the tablet in an amount to create a basic tablet excipient pH of 8.0 or higher, of 8.2 or higher, of 8.5 or higher, or of 8.75 or higher when the combination of excipients employed in the tablet without the mesalamine and without any coating material is placed in a 50 mL volumetric flask, mixed with sufficient water to volume (i.e., 50 mL);
(d) optionally one or more pharmaceutical excipients selected from the group consisting of a binder, a filler, a lubricant, a glidant, a solubilizing agent, a plasticizer, a coloring agent, an antioxidant, a chelating agent, or combinations thereof; and
(e) a delayed release or enteric coating surrounding the tablet;
wherein the tablet exhibits an in vitro release profile before and after storage of the tablet, in an opaque child-resistant screw capped HDPE bottle with or without an aluminum foil seal, at 40° C. and 75% relative humidity for at least 84 days or longer that differs by no more than 20 percentage points, by no more than 15 percentage points, by no more than 12 percentage points, and by no more than 10 percentage points at 1 hour, 2 hours, 3 hours, and/or 4 hours of testing when tested with a USP Apparatus II (paddle), 900-1,000 mL of an aqueous phosphate buffer with a pH of 7.2, 37° C., and 100 rpm.

In an alternative aspect of this embodiment the tablet exhibits a similarity factor ($f_2$) of the in vitro drug release profile before and after storage of 50 or greater, of 55 or greater, of 60 or greater, of 65 or greater, or of 70 or greater.

The following compositions are provided by way of example only and are by no means intended to be limiting.

Example 1

Mesalamine tablets in accordance with the present invention are prepared as follows:

The tablet cores are prepared by sifting 12 grams of sodium carboxymethylcellulose and 3 grams of sodium starch glycolate through an ASTM #30 mesh sieve. The sieved sodium carboxymethylcellulose and sodium starch glycolate are blended with 360 grams of mesalamine to create a mesalamine blend.

6 grams of disodium hydrogen phosphate are dissolved in 180 grams of purified water to create a granulation solution.

The mesalamine blend is granulated with the granulation solution using a KitchenAid mixer. The mesalamine granules are collected and dried in an oven at 60° C.±5° C. until the loss on drying (LOD) at 105° C. was less than 1.5% w/w.

The dried mesalamine granules where sieved using a FitzMill L1A equipped with a 16 mesh sieve. The dried and sieved mesalamine granules were blended with 4.5 grams of magnesium stearate and compressed into tablets using a 20.5×9.5 mm punch.

A delayed release coating was applied to the tablets as follows:

The delayed release coating was prepared as follows:

52.5 grams of Eudragit S 100, 97.5 grams of Eudragit L 100 and 18 grams of triethylcitrate were dissolved in 1014 grams of ethanol to create an enteric coating solution.

37.5 grams of talc, 14 grams of titanium dioxide and 7.5 grams of ferric oxide red were dispersed in 448 grams of ethanol using a homogenizer to create an excipient dispersion.

The enteric coating solution was added to the excipient dispersion to create a delayed release coating suspension which was applied to samples of the mesalamine tablets until a weight gain of about 5.3% w/w was obtained. The delayed release coating was applied using an Automatic tablet coater, model YC-FC-40, with the conditions:

| | |
|---|---|
| Atomizing Air Pressure | 120 NL/min; |
| Inlet Air Temperature | 28-32° C.; |
| Product Temperature | 29-31° C.; |
| Exhaust Air Temperature | 28-31° C.; |
| Spray Rate | 12-14 g/min; |
| Pan Speed | 4-9 rpm |

The coated tablets were dried in an oven at 40° C.±5° C. until the loss on drying (LOD) at 105° C. was less than 1.5% w/w.

The delayed release coated tablets had the following composition:

| Ingredient | Mg/tablet |
|---|---|
| Mesalamine | 1200.0 |
| Sodium Carboxymethycellulose (Na-CMC) Cellulose Gum type: 7H3SXF | 40.0 |
| Disodium Hydrogen Phosphate | 20.0 |
| Sodium Starch Glycolate | 10.0 |
| Magnesium Stearate | 15.0 |
| Total core | 1285.0 |
| Delayed Release Coating | |
| Eudragit S 100 | 15.9 |
| Eudragit L 100 | 29.5 |
| Triethyl Citrate | 5.4 |
| Talc | 11.3 |
| Titanium Dioxide | 4.2 |
| Ferric Oxide Red | 2.3 |
| Total | 1353.6 |

Example 2

Mesalamine tablets in accordance with the present invention are prepared as follows:

The tablet cores are prepared by sifting 10.5 grams of sodium carboxymethylcellulose and 2.1 grams of sodium starch glycolate through an ASTM #30 mesh sieve. The sieved sodium carboxymethylcellulose and sodium starch glycolate are blended with 840 grams of mesalamine to create a mesalamine blend.

5.6 grams of disodium hydrogen phosphate are dissolved in 350 grams of purified water to create a granulation solution.

The mesalamine blend is granulated with the granulation solution using a high shear mixer. The mesalamine granules are collected and dried in an oven at 60° C.±5° C. until the loss on drying (LOD) at 105° C. was less than 1.5% w/w.

The dried mesalamine granules where sieved using a Quadro Comil equipped with a 10 mesh sieve. The dried and sieved mesalamine granules were blended with 10.5 grams of magnesium stearate and compressed into tablets using a 20.5×9.5 mm punch.

A delayed release coating was applied to the tablets as follows:

The delayed release coating was prepared as follows:

50.4 grams of Eudragit S 100, 117.6 grams of Eudragit L 100 and 21.84 grams of triethylcitrate were dissolved in 1092 grams of ethanol to create an enteric coating solution.

42.0 grams of talc, 15.75 grams of titanium dioxide and 8.4 grams of ferric oxide red were dispersed in 468 grams of ethanol using a homogenizer to create an excipient dispersion.

The enteric coating solution was added to the excipient dispersion to create a delayed release coating suspension which was applied to samples of the mesalamine tablets until a weight gain of about 6.8% w/w was obtained. The delayed release coating was applied using an Automatic tablet coater, model YC-FC-40, with the conditions:

| | |
|---|---|
| Atomizing Air Pressure | 120 NL/min; |
| Inlet Air Temperature | 28-32° C.; |
| Product Temperature | 29-31° C.; |
| Exhaust Air Temperature | 28-31° C.; |
| Spray Rate | 15-17 g/min; |
| Pan Speed | 3-10 rpm |

The coated tablets were dried in the coater at inlet air temperature 50° C.±5° C. until the loss on drying (LOD) at 105° C. was less than 1.5% w/w.

The delayed release coated tablets had the following composition:

| Ingredient | Mg/tablet |
|---|---|
| Mesalamine | 1200.0 |
| Sodium Carboxymethycellulose (Na-CMC) Cellulose Gum type: 7H4XF | 15.0 |
| Disodium Hydrogen Phosphate | 8.0 |
| Sodium Starch Glycolate | 3.0 |
| Magnesium Stearate | 15.0 |
| Total core | 1241.0 |
| Delayed Release Coating | |
| Eudragit S 100 | 16.7 |
| Eudragit L 100 | 38.9 |
| Triethyl Citrate | 7.2 |
| Talc | 13.9 |
| Titanium Dioxide | 5.2 |
| Ferric Oxide Red | 2.8 |
| Total | 1325.7 |

Example 3

Samples of the delayed release coated tablets of Example 1 and samples of the commercially available 1200 mg mesalamine tablets, LIALDA® were stored in 125 cc white child resistant screw capped HDPE bottles with an aluminum foil seal for 1, 3 and 6 months at 40° C. and 75% relative humidity and/or 3 months at 30° C. and 75% relative humidity. The tablets of Example 1 and the LIALDA® product were tested using a USP Apparatus II (paddle) at 37° C., 100 rpm wherein the dissolution medium for the first 2 hours is 750 mL of 0.1 N HCl followed by 1 hour using 950 mL of a pH 6.4 phosphate buffer and the remaining time in 960 mL of a pH 7.2 phosphate buffer and the following values were obtained:

| Example 1 | | | | | |
|---|---|---|---|---|---|
| | | Initial | 40°C., 1M | 40°C., 3M | 30°C., 3M |
| | $f_2$ | — | 69.3 | 53.1 | 77.3 |
| 0.1N HCl | 0 | 0.0 | 0.0 | 0.0 | 0.0 |
| | 2 | 0.0 | 0.0 | 0.0 | 0.1 |
| pH 6.4 | 3 | 0.0 | 0.3 | 0.0 | 0.1 |
| pH 7.2 | 4 | 14.6 | 17.4 | 20.9 | 16.7 |
| | 5 | 37.4 | 42.7 | 50.9 | 40.7 |
| | 6 | 62.4 | 69.2 | 76.1) | 66.7 |
| | 7 | 84.7 | 90.1 | 95.2 | 88.2 |
| | 8 | 99.3 | 98.9 | 98.1 | 97.3 |

| LIALDA ® (Lot.5215948) | | | | | |
|---|---|---|---|---|---|
| | | Initial | 40°C., 1M | 40° C., 3M | 30° C., 3M |
| | $f_2$ | — | 36.7 | 26.6 | 40.6 |
| 0.1N HCl | 0 | 0.0 | 0.0 | 0.0 | 0.0 |
| | 2 | 0.0 | 0.0 | 0.0 | 0.0 |
| pH 6.4 | 3 | 0.0 | 0.0 | 0.0 | 0.0 |
| pH 7.2 | 4 | 7.3 | 13.2 | 22.3 | 11.1 |
| | 5 | 20.9 | 40.9 | 64.7 | 36.2 |
| | 6 | 41.2 | 71.7 | 91.3 | 68.1 |
| | 7 | 65.0 | 93.7 | 99.9 | 89.0 |
| | 8 | 86.3 | 99.5 | 98.2 | 96.7 |

| LIALDA ® (Lot.4580828) | | | | | |
|---|---|---|---|---|---|
| | | Initial | 40° C., 1M | 40° C., 3M | 40° C., 6M |
| | $f_2$ | — | 49.5 | 37.9 | 34.7 |
| 0.1N HCl | 0 | 0.0 | 0.0 | 0.0 | 0.0 |
| | 2 | 0.0 | 0.0 | 0.0 | 0.0 |
| pH 6.4 | 3 | 0.0 | 0.0 | 0.0 | 0.0 |
| pH 7.2 | 4 | 11.5 | 13.9 | 31.1 | 33.5 |
| | 5 | 39.2 | 58.2 | 71.0 | 75.8 |
| | 6 | 74.3 | 89.9 | 94.8 | 98.5 |
| | 7 | 97.1 | 100.4 | 101.2 | 102.6 |

The difference in release values before and after storage in the pH 7.2 phosphate buffer media can be summarized as follows:

Example 1

| pH 7.2 time | 40° C. 1 month | 40° C. 3 months | 30° C. 3 months |
|---|---|---|---|
| 1 hour | 2.8 | 6.3 | 2.1 |
| 2 hours | 5.3 | 13.5 | 3.3 |
| 3 hours | 6.8 | 13.7 | 4.3 |
| 4 hours | 5.4 | 10.5 | 3.5 |

| LIALDA ® (Lot 5215948) | | | |
|---|---|---|---|
| pH 7.2 time | 40° C. 1 month | 40° C. 3 months | 30° C. 3 months |
| 1 hour | 5.9 | 15.0 | 3.8 |
| 2 hours | 20.0 | 43.8 | 15.3 |
| 3 hours | 30.5 | 50.1 | 26.9 |
| 4 hours | 28.7 | 34.9 | 24.0 |

| LIALDA ® (Lot 4580828) | | | |
|---|---|---|---|
| pH 7.2 time | 40° C. 1 month | 40° C. 3 months | 40° C. 6 months |
| 1 hour | 2.4 | 19.6 | 22.0 |
| 2 hours | 19.0 | 31.8 | 36.6 |
| 3 hours | 15.6 | 20.5 | 24.2 |

The package insert for the LIALDA® product indicates the product contains the following ingredient: mesalamine, carboxymethylcellulose sodium, carnauba wax, stearic acid, silica (colloidal hydrated), sodium starch glycolate, talc, magnesium stearate, methacrylic acid copolymer, triethyl citrate, titanium dioxide, red ferric oxide and polyethylene glycol 6000.

Example 4

Samples of the delayed release coated tablets of Example 2, samples of the commercially available 1200 mg mesalamine tablet, LIALDA® and samples of a commercially available 1200 mg mesalamine tablet sold by Zydus Pharmaceuticals USA Inc. (hereinafter "Zydus product") were stored in 125 cc white child resistant screw capped HDPE bottles with an aluminum foil seal for 2 days at 60° C. and 75% relative humidity. The tablets of Example 2, the LIALDA® product and the Zydus product were tested using a USP Apparatus II (paddle) at 37° C., 100 rpm wherein the dissolution medium for the first 2 hours is 750 mL of 0.1 N HCl followed by 1 hour using 950 mL of a pH 6.4 phosphate buffer and the remaining time in 960 mL of a pH 7.2 phosphate buffer and the following values were obtained:

| | | Initial | | 60° C., 2 days | |
|---|---|---|---|---|---|
| | | Example 2 | Zydus Product | Example 2 | Zydus Product |
| 0.1N HCl | 0 | 0.0 | 0.0 | 0.0 | 0.0 |
| | 2 | 0.0 | 0.0 | 0.0 | 0.0 |
| pH 6.4 | 3 | 0.0 | 0.0 | 0.0 | 0.0 |
| pH 7.2 | 4 | 10.8 | 10.1 | 8.0 | 15.8 |
| | 5 | 34.9 | 34.3 | 31.5 | 45.5 |
| | 6 | 63.2 | 61.4 | 59.3 | 72.4 |
| | 7 | 86.2 | 81.7 | 85.6 | 91.8 |
| | 8 | 93.6 | 93.9 | 95.5 | 98.4 |

The package insert for the Zydus product indicates the product contains the following ingredients: mesalamine, carboxymethylcellulose sodium, colloidal silicon dioxide, sodium starch glycolate, talc, magnesium stearate, methacrylic acid copolymer, triethyl citrate, titanium dioxide, iron oxide red, polyethylene glycol, hypromellose, iron oxide yellow and microcrystalline cellulose.

| LIALDA ® tablets | | | | | | | |
|---|---|---|---|---|---|---|---|
| | | | Initial | | | 60° C., 2 days | |
| Lot. | | 4580828 | 4752178 | 5215948 | 4580828 | 4752178 | 5215948 |
| | $f_2$ | — | — | — | 50.2 | 52.4 | 43.4 |
| 0.1N HCl | 0 | 0.0 | 0.0 | 0.0 | 0.0 | 0.0 | 0.0 |
| | 2 | 0.0 | 0.0 | 0.0 | 0.0 | 0.0 | 0.0 |
| pH 6.4 | 3 | 0.1 | 0.0 | 0.0 | 0.0 | 0.0 | 0.0 |
| pH 7.2 | 4 | 11.5 | 8.7 | 8.3 | 17.3 | 12.0 | 12.5 |
| | 5 | 39.2 | 34.0 | 28.2 | 57.3 | 48.5 | 49.1 |
| | 6 | 74.3 | 67.5 | 55.0 | 89.1 | 83.2 | 79.6 |
| | 7 | 97.1 | 93.5 | 82.3 | 98.2 | 96.3 | 97.1 |
| | 8 | — | 99.8 | 97.1 | — | 100.6 | 99.6 |

The difference in release values between the tablets of Example 2 and the LIALDA® product before and after storage in the pH 7.2 phosphate buffer media can be summarized as follows:

| pH 7.2 time | Ex. 2 | LIALDA ® (4580828) | LIALDA ® (4752178) | LIALDA ® (5215948) |
|---|---|---|---|---|
| 1 hour | −2.8 | 5.8 | 3.3 | 4.2 |
| 2 hour | −3.4 | 18.1 | 14.5 | 20.9 |
| 3 hour | −3.9 | 14.8 | 15.7 | 24.6 |
| 4 hour | −0.6 | 1.1 | 2.8 | 14.8 |

Example 5

Uncoated mesalamine tablets in accordance with the present invention are prepared according to the procedure outlined in Examples 1 and 2 and the uncoated tablets had the following composition:

| Ingredient | Mg/tablet |
|---|---|
| Mesalamine | 1200 |
| Sodium Carboxymethycellulose (Na-CMC) Cellulose Gum type: 7H3SXF | 40 |
| Disodium Hydrogen Phosphate | 30 |
| Sodium Starch Glycolate | 10 |
| Magnesium Stearate | 10 |
| Total | 1290 |

Example 6

Uncoated mesalamine tablets in accordance with the present invention are prepared according to the procedure outlined in Examples 1 and 2 and the uncoated tablets had the following composition:

| Ingredient | Mg/tablet |
|---|---|
| Mesalamine | 1200 |
| Sodium Carboxymethycellulose (Na-CMC) Cellulose Gum type: 7H3SXF | 40 |
| L-arginine | 10 |
| Sodium Starch Glycolate | 10 |
| Magnesium Stearate | 10 |
| Total | 1270 |

Example 7

Uncoated mesalamine tablets in accordance with the present invention are prepared according to the procedure outlined in Examples 1 and 2 and the uncoated tablets had the following composition:

| Ingredient | Mg/tablet |
|---|---|
| Mesalamine | 1200 |
| Sodium Carboxymethycellulose (Na-CMC) Cellulose Gum type: 7H3SXF | 40 |
| Sodium Citrate | 30 |
| Sodium Starch Glycolate | 10 |
| Magnesium Stearate | 10 |
| Total | 1290 |

Example 8

Uncoated mesalamine tablets not in accordance with the present invention are prepared according to the procedure outlined in Examples 1 and 2 and the uncoated tablets had the following composition:

| Ingredient | Mg/tablet |
|---|---|
| Mesalamine | 1200 |
| Sodium Carboxymethycellulose (Na-CMC) Cellulose Gum type: 7H3SXF | 40 |
| Sodium Starch Glycolate | 10 |
| Magnesium Stearate | 10 |
| Total | 1260 |

Example 9

Samples of the uncoated tablets of Examples 5-8 were stored in child resistant screw capped HDPE bottles with an aluminum foil seal for 2 days at 60° C. and 75% relative humidity. The tablets of Examples 5-8 were tested using a USP Apparatus II (paddle) at 37° C., 100 rpm, 960 mL of pH 7.2 phosphate buffer and the following values were obtained:

|  | Initial | | | | 60° C., 2 days | | | |
|---|---|---|---|---|---|---|---|---|
|  | Ex. 5 | Ex. 6 | Ex. 7 | Ex. 8 | Ex. 5 | Ex. 6 | Ex. 7 | Ex. 8 |
| $f_2$ | — | — | — | — | 70.1 | 56.0 | 55.5 | 29.2 |
| 0 hour | 0.0 | 0.0 | 0.0 | 0.0 | 0.0 | 0.0 | 0.0 | 0.0 |
| 0.5 hour | 8.5 | 8.1 | 9.7 | 6.9 | 10.6 | 7.8 | 12.3 | 11.4 |
| 1 hour | 18.6 | 16.3 | 18.6 | 14.3 | 22.6 | 16.0 | 24.5 | 28.9 |
| 2 hour | 48.5 | 38.7 | 45.3 | 35.7 | 52.6 | 36.7 | 54.6 | 78.0 |
| 3 hour | 75.0 | 62.9 | 73.9 | 61.1 | 79.0 | 56.0 | 87.0 | 98.1 |
| 4 hour | 94.4 | 92.3 | 99.9 | 97.2 | 98.7 | 77.1 | 100.2 | 98.6 |
| 5 hour | 98.1 | 98.8 | 100.6 | 98.5 | 101.5 | 98.9 | 100.7 | 99.1 |

The difference in release values before and after storage can be summarized as follows:

|  | Ex. 5 | Ex. 6 | Ex. 7 | Ex. 8 |
|---|---|---|---|---|
| 0.5 hour | 2.0 | −0.3 | 2.6 | 4.5 |
| 1 hour | 4.0 | −0.3 | 5.9 | 14.6 |
| 2 hour | 4.1 | −2.0 | 9.3 | 42.3 |
| 3 hour | 4.0 | −6.9 | 13.1 | 37 |
| 4 hour | 4.3 | −15.2 | 0.3 | 1.4 |

Example 10

Uncoated mesalamine tablets in accordance with the present invention are prepared according to the procedure outlined in Examples 1 and 2 and the uncoated tablets had the following composition:

| Ingredient | Mg/tablet |
|---|---|
| Mesalamine | 1200.0 |
| Sodium Carboxymethycellulose (Na-CMC) Cellulose Gum type: 7H3SXF | 40.0 |
| Disodium Hydrogen Phosphate | 60.0 |
| Sodium Starch Glycolate | 10.0 |
| Magnesium Stearate | 10.0 |
| Total | 1320 |

Samples of the uncoated tablets of this Example were stored in child resistant screw capped HDPE bottles with an aluminum foil seal for 2 days at 60° C. and 75% relative humidity. The tablets were tested using a USP Apparatus II (paddle) at 37° C., 100 rpm, 960 mL of pH 7.2 phosphate buffer and the following mean values were obtained:

|  | Initial | 60° C., 2 days | Change |
|---|---|---|---|
| 0 hour | 0.0 | 0.0 | 0.0 |
| 0.5 hour | 12.8 | 16.1 | 3.3 |
| 1 hour | 24.8 | 29.4 | 4.6 |
| 2 hour | 51.5 | 57.3 | 5.8 |
| 3 hour | 75.4 | 80.3 | 4.9 |
| 4 hour | 94.6 | 97.0 | 2.4 |
| 5 hour | 100.0 | 100.0 | 0.0 |

The $f_2$ value was calculated as 67.4.

Example 11

Uncoated mesalamine tablets in accordance with the present invention are prepared according to the procedure outlined in Examples 1 and 2 and the uncoated tablets had the following composition:

| Ingredient | Mg/tablet |
|---|---|
| Mesalamine | 1200.0 |
| Sodium Carboxymethycellulose (Na-CMC) Cellulose Gum type: 7H3SXF | 40.0 |
| L-Arginine | 5.0 |
| Sodium Starch Glycolate | 10.0 |
| Magnesium Stearate | 10.0 |
| Total | 1265 |

Samples of the uncoated tablets of this Example were stored in child resistant screw capped HDPE bottles with an aluminum foil seal for 2 days at 60° C. and 75% relative humidity. The tablets were tested using a USP Apparatus II (paddle) at 37° C., 100 rpm, 960 mL of pH 7.2 phosphate buffer and the following mean values were obtained:

|  | Initial | 60° C., 2 days | Change |
|---|---|---|---|
| 0 hour | 0.0 | 0.0 | 0.0 |
| 0.5 hour | 7.1 | 9.2 | 2.1 |
| 1 hour | 14.6 | 19.0 | 4.4 |
| 2 hour | 34.7 | 42.6 | 7.9 |
| 3 hour | 57.8 | 66.9 | 9.1 |
| 4 hour | 82.8 | 96.4 | 13.6 |
| 5 hour | 99.5 | 99.6 | 0.1 |

The $f_2$ value was calculated as 55.6.

Example 12

The following excipient compositions were prepared by weighing each excipient and transferring them into a 50 mL volumetric flask:

| Ingredient | Sample A | Sample B | Sample C |
|---|---|---|---|
| Sodium carboxymethycellulose (7H3SXF) | 80.0 mg | 80.0 mg | 80.0 mg |
| Sodium Starch Glycolate | 20.0 mg | 20.0 mg | 20.0 mg |
| Magnesium Stearate | 20.0 mg | 20.0 mg | 20.0 mg |
| L-Arginine | — | 20.0 mg | — |
| Disodium Hydrogen Phosphate | — | — | 120 mg |

Deionized water was added to each volumetric flask to volume and stirred for 15 minutes. After stirring, the contents were passed through a 0.45 μm filter and the pH of the filtrate was measured as follows:

Sample A=7.67
Sample B=10.16
Sample C=8.91

The excipient in Sample A correspond to the excipients in Example 8.

The excipient in Sample B correspond to the excipients in Example 6.

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A mesalamine tablet comprising:
(i) about 70 wt % to about 97 wt % of mesalamine;
(ii) about 1 wt % to about 20 wt % of a controlled release excipient selected from carboxymethylcellulose calcium, carboxymethylcellulose sodium, or mixtures thereof;
(iii) about 0.1 wt % to about 7.5 wt % of a buffering/basifying agent selected from the group consisting of arginine, lysine, boric acid, calcium carbonate, calcium hydroxide, calcium lactate, calcium phosphate, diethanolamine, methionine, monoethanolamine, monosodium glutamate, meglumine, potassium acetate, potassium bicarbonate, potassium borate, potassium carbonate, potassium citrate, potassium hydroxide, potassium lactate, potassium phosphate, sodium acetate, sodium bicarbonate, sodium borate, sodium carbonate, sodium citrate, sodium hydroxide, sodium lactate, sodium phosphate, triethanolamine, or combinations thereof, wherein the buffering/basifying agent is present in the tablet in an amount to create a basic tablet excipient pH of 8.0 or higher when the combination of excipients employed in the tablet without the mesalamine and without any coating material is placed in a 50 mL volumetric flask, mixed with sufficient water to a volume of 50 mL;

(iv) optionally one or more pharmaceutical excipients selected from the group consisting of a binder, a filler, a lubricant, a glidant, a solubilizing agent, a plasticizer, a coloring agent, an antioxidant, a chelating agent, or combinations thereof; and (v) optionally a delayed release or enteric coating surrounding the tablet;

wherein the tablet exhibits an in vitro release profile before and after storage of the tablet, in an opaque child-resistant screw capped high density polyethylene bottle with an aluminum foil seal, at 40° C. and 75% relative humidity for at least 28 days increases by no more than 20 percentage points, at 1 hour, 2 hours, 3 hours, and 4 hours of testing when tested with a USP Apparatus II (paddle), 900-1,000 mL of an aqueous phosphate buffer with a pH of 7.2, 37° C., and 100 rpm.

2. The mesalamine tablet as described in claim 1 wherein the tablet exhibits a similarity factor ($f_2$) of the in vitro drug release profile before and after storage of 50 or greater.

3. The mesalamine tablet of claim 1 wherein the buffering/basifying agent is selected from the group consisting of disodium hydrogen phosphate, arginine, sodium citrate, potassium hydroxide, sodium hydroxide or a mixture thereof.

4. The mesalamine tablet of claim 1 comprising the delayed release or enteric coating surrounding the tablet.

5. A mesalamine tablet comprising:
(i) about 70 wt % to about 97 wt % of mesalamine;
(ii) about 1 wt % to about 20 wt % of a controlled release excipient selected from carboxymethylcellulose calcium, carboxymethylcellulose sodium, or mixtures thereof;
(iii) about 0.1 wt % to about 7.5 wt % of a buffering/basifying agent selected from the group consisting of disodium hydrogen phosphate, arginine, sodium citrate, potassium hydroxide, sodium hydroxide or a mixture thereof, and the buffering/basifying agent is present in the tablet in an amount to create a basic tablet excipient pH of 8.0 or higher when the combination of excipients employed in the tablet without the mesalamine and without any coating material is placed in a 50 mL volumetric flask, mixed with sufficient water to a volume of 50 mL;
(iv) optionally one or more pharmaceutical excipients selected from the group consisting of a binder, a filler, a lubricant, a glidant, a solubilizing agent, a plasticizer, a coloring agent, an antioxidant, a chelating agent, or combinations thereof; and
(v) optionally a delayed release or enteric coating surrounding the tablet;

wherein the tablet exhibits an in vitro release profile before and after storage of the tablet, in an opaque child-resistant screw capped high density polyethylene bottle with an aluminum foil seal, at 40° C. and 75% relative humidity for at least 28 days increases by no more than 20 percentage points, at 1 hour, 2 hours, 3 hours, and 4 hours of testing when tested with a USP Apparatus II (paddle), 900-1000 mL of an aqueous phosphate buffer with a pH of 7.2, 37° C., and 100 rpm.

6. The mesalamine tablet of claim 5 comprising the delayed release or enteric coating surrounding the tablet.

* * * * *